United States Patent
Fasanmade

(10) Patent No.: US 12,303,724 B2
(45) Date of Patent: May 20, 2025

(54) NON-ADULT HUMAN DOSING OF ANTI-CD30 ANTIBODY-DRUG CONJUGATES FOR TREATMENT OF HEMATOLOGICAL OR LYMPHOID CANCER

(71) Applicant: Takeda Pharmaceutical Company Limited, Osaka (JP)

(72) Inventor: Adedigbo Fasanmade, Cambridge, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 448 days.

(21) Appl. No.: 17/902,240

(22) Filed: Sep. 2, 2022

(65) Prior Publication Data

US 2023/0136346 A1 May 4, 2023

Related U.S. Application Data

(63) Continuation of application No. 16/349,499, filed as application No. PCT/US2017/061294 on Nov. 13, 2017, now Pat. No. 11,464,869.

(60) Provisional application No. 62/421,527, filed on Nov. 14, 2016.

(51) Int. Cl.
| | |
|---|---|
| *A61P 35/00* | (2006.01) |
| *A61K 31/475* | (2006.01) |
| *A61K 31/573* | (2006.01) |
| *A61K 31/655* | (2006.01) |
| *A61K 31/675* | (2006.01) |
| *A61K 31/704* | (2006.01) |
| *A61K 39/00* | (2006.01) |
| *A61K 39/395* | (2006.01) |
| *A61K 45/06* | (2006.01) |
| *A61K 47/68* | (2017.01) |
| *A61P 35/02* | (2006.01) |
| *C07K 16/28* | (2006.01) |

(52) U.S. Cl.
CPC ........ *A61K 47/6889* (2017.08); *A61K 31/475* (2013.01); *A61K 31/573* (2013.01); *A61K 31/655* (2013.01); *A61K 31/675* (2013.01); *A61K 31/704* (2013.01); *A61K 39/39558* (2013.01); *A61K 45/06* (2013.01); *A61K 47/68031* (2023.08); *A61K 47/6811* (2017.08); *A61K 47/6817* (2017.08); *A61K 47/6849* (2017.08); *A61K 47/6851* (2017.08); *A61P 35/00* (2018.01); *A61P 35/02* (2018.01); *C07K 16/2878* (2013.01); *A61K 2039/505* (2013.01); *A61K 2039/545* (2013.01); *A61K 2039/55* (2013.01); *C07K 2317/24* (2013.01); *C07K 2317/90* (2013.01); *C07K 2317/94* (2013.01)

(58) Field of Classification Search
CPC .............................. A61P 35/00; A61P 35/02
See application file for complete search history.

(56) References Cited

U.S. PATENT DOCUMENTS

| | | |
|---|---|---|
| 11,464,869 B2 | 10/2022 | Fasanmade |
| 2019/0290776 A1 | 9/2019 | Fasanmade |

FOREIGN PATENT DOCUMENTS

| | | |
|---|---|---|
| CN | 104998273 A | 10/2015 |
| CN | 105764516 A | 7/2016 |
| CN | 105992595 A | 10/2016 |
| JP | 2009-501800 A | 1/2009 |
| WO | WO 2007/011968 A2 | 1/2007 |
| WO | WO 2015/085289 A1 | 6/2015 |
| WO | WO 2017/137458 A1 | 8/2017 |

OTHER PUBLICATIONS

Advani et al., BrentuximabVedotin (SGN-35) in Patients with Relapsed or Refractory Systemic Anaplastic Large Cell Lymphoma: A Phase 2 Study Update. Blood. Nov. 2011; 118(21): 443. https://doi.org/10.1182/blood.V118.21.443.443.

Chen et al., Targeted therapy for Hodgkin lymphoma and systemic anaplastic large cell lymphoma: focus on brentuximab vedotin. Onco Targets Ther. Dec. 19, 2013;7:45-56. doi: 10.2147/OTT.S39107.

Fanale et al., Complete Remissions Observed in a Subset of Pediatric Patients With CD30-expressing Malignant Lymphomas Treated in Clinical Studies of Brentuximab Vedotin (SGN-35). European Journal of Cancer. 2011; 47(1):S640.

Flerlage et al., Pharmacokinetics, immunogenicity, and safety of weekly dosing of brentuximab vedotin in pediatric patients with Hodgkin lymphoma. Cancer Chemother Pharmacol. Dec. 2016;78(6):1217-1223. doi: 10.1007/s00280-016-3180-x. Epub Nov. 11, 2016.

Furqan et al., Surface area in children: a simple formula. Indian Pediatr. Dec. 2009;46(12): 1085-7. Epub Apr. 1, 2009.

Locatelli et al., Phase 1/2 study of brentuximab vedotin in pediatric patients with relapsed or refractory (R/R) Hodgkin lymphoma (HL) or systemic anaplastic large-cell lymphoma (SALCL): Preliminary phase 2 data for Brentuximab vedotin 1.8 mg/kg in the HL study arm. 55th Annual Meeting of American Society of Hematology (ASH). New Orleans, LA, United States. Dec. 7, 2013. 3 pages.

(Continued)

*Primary Examiner* — Elly-Gerald Stoica

(74) *Attorney, Agent, or Firm* — Wolf, Greenfield & Sacks, P.C.

(57) ABSTRACT

The invention provides, inter alia, methods of treating a disorder characterized by pathological activity of CD30+ cells, such as in certain solid, hematological and lymphoid cancers, in a non-adult human subject by administering an effective amount of an anti-CD30 ADC (antibody drug conjugate), such as, brentuximab vedotin, to the subject. The invention also provides corresponding kits and articles of manufacture suitable for performing the methods provided by the invention.

14 Claims, 1 Drawing Sheet

(56) References Cited

OTHER PUBLICATIONS

Moriyama et al., Growth Of Children And Evaluation Of Pediatric Dose Based On Body Surface Area. Journal of the Nippon Hospital Pharmacists Association. 1992; 18(3): 245-251.

No Author Listed, Adcetrist (brentuximab vedotin) Highlights of Prescribing Information. Retrieved from: https://www.accessdata.fda.gov/drugsatfda_docs/label/2011/125388s000, 125399s000lbl.pdf. Aug. 2011. 15 pages.

No Author Listed, Data table of weight-for-age charts. CDC. Aug. 2001. Retrieved from: HTTPS://www.cdc.gov/growthcharts, [last reviewed: Aug. 23, 2001].

No Author Listed, Erbitux (cetuximab) Highlights of Prescribing Information. U.S. Food and Drug Administration. Retrieved from: Accessdata.fda.gov. 2004. 21 pages.

No Author Listed, Guidance for Industry—Estimating the Maximum Safe Starting Dose in Initial Clinical Trials for Therapeutics in Adult Healthy Volunteers. U.S. Dept. of Health and Human Services. Jul. 2005. 30 pages.

Pinkel, The use of body surface area as a criterion of drug dosage in cancer chemotherapy. Cancer Res. Aug. 1958;18(7):853-6.

Redlarski et al., Body surface formulae: an alarming ambiguity. Sci Rep. Jun. 21, 2016;6:27966. doi: 10.1038/srep27966.

Shi et al., Pediatric dosing and body size in biotherapeutics. Pharmaceutics. Dec. 16, 2010;2(4):389-418. doi: 10.3390/pharmaceutics2040389.

Sorge et al., Targeted Therapies for the Treatment of Pediatric Non-Hodgkin Lymphomas: Present and Future. Pharmaceuticals (Basel). May 19, 2016;9(2):28. doi: 10.3390/ph9020028.

Suri et al., Population Pharmacokinetics of Brentuximab Vedotin in Adult and Pediatric Patients With Relapsed/Refractory Hematologic Malignancies: Model-Informed Hypothesis Generation for Pediatric Dosing Regimens. J Clin Pharmacol. Dec. 2020;60(12):1585-1597. doi: 10.1002/jcoh.1682. Eoub Jun. 28, 2020.

Tacyildiz et al., Brentuximab vedotin in heavily treated refractory or relapsed pediatric Hodgkin lymphoma patients who received autologous stem cell transplantation (ASCT), a single Turkish centre study. Bone Marrow Transplantation. 2015; 50(1):S460.

Takeda, Study of Brentuximab Vedotin (SGN-35) in Pediatric Participants With Relapsed or Refractory (r/r) Systemic Anaplastic Large-Cell Lymphoma or Hodgkin Lymphoma. 2017. Accessed from: URL:https://clinicaltrials.gov/ct2/show/record/NCT01492088.

ADCETRIS AUC at 1.8 mg/kg and at 71.5 mg/m² versus Age

NON-ADULT HUMAN DOSING OF ANTI-CD30 ANTIBODY-DRUG CONJUGATES FOR TREATMENT OF HEMATOLOGICAL OR LYMPHOID CANCER

PRIOR APPLICATIONS

This application is a continuation of U.S. patent application Ser. No. 16/349,499, filed May 13, 2019, which is a national stage application under 35 U.S.C. § 371 of PCT/US2017/061294, filed Nov. 13, 2017, which designated the U.S. and claims the benefit of U.S. Provisional Application No. 62/421,527, filed Nov. 14, 2016. The entire disclosure of the foregoing applications are incorporated herein by reference.

FIELD OF THE INVENTION

The present invention relates to methods of treating a disorder characterized by pathological activity of CD30+ cells, such as in certain solid, hematological and lymphoid malignancies, particularly in a non-adult (pediatric) human subject.

BACKGROUND

Traditional, small-molecule drugs are typically dose-adjusted for a non-adult human subject using established methodology, adjusting for the generally higher metabolism of a non-adult human subject. Biologic molecules, however, cannot be as readily dose adjusted for a non-adult subject, because, inter alia, their pharmacokinetics are much more unpredictable than small molecules. Antibody-drug conjugates (ADCs) are therapeutics that typically contain both biologic and small molecule components and thus can exhibit even more unpredictable pharmacokinetics. Anti-CD30 ADCs, such as brentuximab vedotin (BV; tradename ADCETRIS®), provide numerous benefits to adult subjects, e.g., when treating certain solid, hematological, and lymphoid cancers. Brentuximab vedotin is currently approved in the US for treatment of patients with Classical Hodgkin lymphoma (cHL) after failure of autologous hematopoietic stem cell transplantation (auto-HSCT) or after failure of at least two prior multi-agent chemotherapy regimens in patients who are not auto-HSCT candidates, classical HL at high risk of relapse or progression as post-auto-HSCT consolidation, systemic anaplastic large cell lymphoma (sALCL) after failure of at least one prior multi-agent chemotherapy regimen, and Primary cutaneous anaplastic large cell lymphoma (pcALCL) or CD30 expressing mycosis fungoides (MF) who have received prior systemic therapy; and is administered as an intravenous infusion over 30 minutes every 3 weeks at a dose based on body weight in adult human subjects. But in view of the unpredictability of the pharmacokinetics of ADCs like brentuximab vedotin, a need exists for corresponding methods of treating non-adult human subjects.

SUMMARY

The invention provides, inter alia, methods of treating a disorder characterized by pathological activity of CD30+ cells, such as in certain solid, hematological and lymphoid cancers, in a non-adult human subject by administering an effective amount of an anti-CD30 ADC to the subject. The invention is based, at least in part, on Applicant's discovery that a body surface area (BSA)-adjusted dose of an anti-CD30 ADC provides a more consistent exposure to the ADC across non-adult human subjects compared to weight-adjusted doses of an anti-CD30 ADC, as assessed by area under the curve (AUC).

Thus, in one aspect, the invention provides methods of treating a hematological, lymphoid or solid cancer in a non-adult human subject. The methods entail administering one or more doses of an anti-CD30 antibody-drug conjugate (ADC) at a body surface area-adjusted dose.

In some embodiments, the anti-CD30 antibody-drug conjugate (ADC) is administered at a dose of between about: 32-78 mg/m$^2$, e.g., about: 64-78 mg/m$^2$, e.g., between about: 66-76 mg/m$^2$, 68-74 mg/m$^2$, 70-72 mg/m$^2$, or about 71.5 mg/m$^2$, e.g., every three weeks; or e.g., about: 43-53 mg/m$^2$, e.g. between about: 45-51 mg/m$^2$, 47-49 mg/m$^2$ or about 48 mg/m$^2$, e.g., every two weeks; or about 32-40 mg/m$^2$, e.g. between about: 34-38 mg/m$^2$, 35-37 mg/m$^2$, or about 36 mg/m$^2$, e.g. about every two weeks. In some particular embodiments, the anti-CD30 antibody-drug conjugate (ADC) is administered at a dose of between about: 70-72 mg/m$^2$, 71-72 mg/m$^2$, or about 71.5 mg/m$^2$ every three weeks. In some particular embodiments, the anti-CD30 antibody-drug conjugate (ADC) is administered at a dose of between about: 45-51 mg/m$^2$, 47-49 mg/m$^2$ or about 48 mg/m$^2$ every two weeks. In some particular embodiments, the anti-CD30 antibody-drug conjugate (ADC) is administered at dose of between about: 34-38 mg/m$^2$, 35-37 mg/m$^2$ or about 36 mg/m$^2$ every two weeks. In certain particular embodiments, the anti-CD30 antibody-drug conjugate (ADC) is administered at a dose of about 71.5 mg/m$^2$ or about 78 mg/m$^2$. In other certain embodiments, the anti-CD30 antibody-drug conjugate (ADC) is administered at a dose of about 43 mg/m$^2$, or about 48 mg/m$^2$. In still other certain embodiments, the anti-CD30 antibody-drug conjugate (ADC) is administered at a dose of about 36 mg/m$^2$.

In certain embodiments, the subject is undergoing concurrent chemotherapy, such as AVD (adriamycin, vinblastine, dacarbazine), CHP (doxorubicin, cyclophosphamide, prednisone), RCHOP (doxorubicin, cyclophosphamide, prednisone, vincristine), rituximab+bendamustine, or immunotherapy (including one or more checkpoint inhibitors, such as nivolumab); HSC (hematopoietic stem cell) transplant therapy; radio therapy; or a combination thereof.

In some embodiments, the subject's normalized drug expose as measured by area under the ADC concentration time curve (AUC) is substantially similar to an adult AUC for an indicated adult dose.

In certain embodiments, the ADC comprises an anti-CD30 antibody comprising the complementarity determining regions (CDRs) of cACIO. In more particular embodiments, the ADC comprises the anti-CD30 antibody cACIO. In certain particular embodiments, the ADC comprises an auristatin. In more particular embodiments, the auristatin is monomethyl auristatin E (MMAE). In some embodiments, the ADC comprises a cathepsin cleavable linker, optionally including a spacer. In more particular embodiments, the cathepsin cleavable linker is a valine-citrulline linker. In still more particular embodiments, the ADC is brentuximab vedotin.

In some embodiments of the invention, the ADC is administered for more than one cycle, e.g., 2, 3, 4, 5, 6, 7, 8, 9, 10, 11, 12, 13, 14, 15, 16, 17, 18, 19, or 20, or more, cycles, e.g., once every one, two, three, four, five, or six weeks, e.g., once every two or three weeks.

In a related aspect, the invention provides an anti-CD30 antibody-drug conjugate (ADC) at a body surface-area adjusted dose suitable for treating a non-adult human subject, e.g., for treating a hematological, lymphoid or solid cancer.

In another aspect, the invention provides methods of treating a hematological, lymphoid or solid cancer in a non-adult human subject by administering one or more doses of brentuximab vedotin to the subject at a dose of between about: 32-78 mg/m$^2$, e.g.: about: 64-78 mg/m$^2$, e.g. between about: 66-76 mg/m$^2$, 68-74 mg/m$^2$, 70-72 mg/m$^2$, or about 71.5 mg/m$^2$, e.g., every three weeks; or e.g., about: 43-53 mg/m$^2$, e.g. between about: 45-51 mg/m$^2$, 47-49 mg/m$^2$ or about 48 mg/m$^2$, e.g., every two weeks; or about 32-40 mg/m$^2$, e.g. between about: 34-38, 35-37, or about 36 mg/m$^2$, e.g. every two weeks.

In yet another embodiment, the invention provides brentuximab vedotin for treating a hematological or lymphoid cancer in a non-adult human subject, where the brentuximab vedotin is provided at a dose of between about: 32-78 mg/m$^2$, e.g.: about: 64-78 mg/m$^2$, e.g. between about: 66-76 mg/m$^2$, 68-74 mg/m$^2$, 70-72 mg/m$^2$, or about 71.5 mg/m$^2$, e.g., every three weeks; or e.g., about: 43-53 mg/m$^2$, e.g. between about: 45-51 mg/m$^2$, 47-49 mg/m$^2$ or about 48 mg/m$^2$, e.g., every two weeks; or about 32-40 mg/m$^2$, e.g. between about: 34-38, 35-37, or about 36 mg/m$^2$, e.g., every two weeks.

DETAILED DESCRIPTION

Figure 1A:
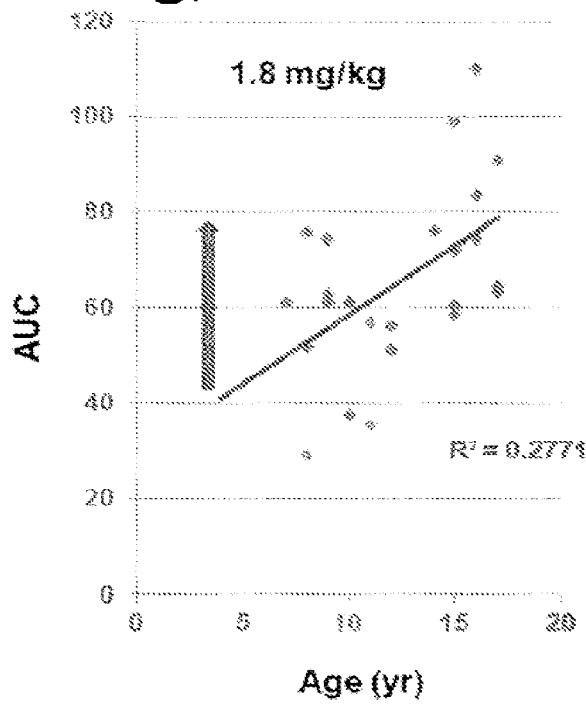
FIGS. 1A-1B are a pair of scatterplots of area under the curve (AUC) of BV versus age for subjects. AUC units are microgram/ml*day.

The invention provides, inter alia, methods of treating a disorder characterized by pathological activity of CD30+ cells, such as in certain solid, hematological and lymphoid cancers in a non-adult human subject. These methods include the step of administering one or more doses of an anti-CD30 antibody-drug conjugate (ADC) at a body surface area-adjusted dose to the subject. In a related aspect, the invention also provides targeted uses (including second medical uses) of anti-CD30 antibody-drug conjugates to provide a body surface area-adjusted dose in the treatment of a disorder characterized by pathological activity of CD30+ cells, such as in certain solid, hematological and lymphoid cancers. These methods, targeted uses, and second medical uses will collectively be referred to as the "methods provided by the invention" or "methods of the invention." In another related aspect, the invention provides kits and articles of manufacture (such as unit or cycle dosage forms) adapted for treating a non-adult human subject, e.g., according to the methods provided by the invention—i.e., at a body surface-area adjusted dose suitable for treating a non-adult human subject, e.g., for a solid, hematological or lymphoid cancer. The kits, and articles of manufacture, in some embodiments, include instructions and/or labeling for use according to any of the methods provided by the invention. Collectively, these are the "kits provided by the invention" and together with the methods provided by the invention are the "kits and methods provided by the invention."

"Anti-CD30" is an immunoglobulin (antibody), or fragment thereof comprising an antigen-binding domain, that specifically binds the antigen CD30. The terms "specific binding" and "specifically binds" mean that the anti-CD30 antibody will react, in a highly selective manner, with its corresponding target, CD30 and not with the multitude of other antigens. Typically, the anti-CD30 antibody binds with an affinity of at least about 1×10$^{-7}$M, and preferably 10$^{-8}$M to 10$^{-9}$M, 10$^{-10}$ M, 10$^{-11}$ or 10$^{-12}$ M. One M, particular antibody that is useful for ADCs useful in methods provided by the invention is the chimeric antibody cAC10 (which is the antibody backbone of brentuximab vedotin), or a related antibody. An antibody that is a "related antibody" (which encompasses a "related antigen-binding fragment") of a reference antibody encompasses antibodies (and antigen-binding fragments thereof) that: compete with the reference antibody for binding the target antigen (e.g., in some embodiments, competition for the same, overlapping, or adjacent epitopes), have the epitopic specificity of the reference antibody, comprise the complementarity determining regions (CDRs) of the reference antibody (in some embodiments, there may be up to 1, 2, 3, 4, or 5 conservative amino acid substitutions in the whole of the CDRs, or up to 1 or 2 conservative substitutions in each CDR), or comprise the variable heavy and variable light domains of the reference antibody (or may have at least 80, 85, 90, 95, 96, 97, 98, 99%, or more amino acid identity to the variable domains, where any amino acid changes are in the framework region and may be conservative or non-conservative). In some embodiments, conservative substitutions are determined by BLASTp's default parameters, while, in other embodiments, conservative mutations are within class substitutions, where the classes are aliphatic (glycine, alanine, valine, leucine, isoleucine), hydroxyl or sulphur/selenium-containing (serine, cysteine, selenocysteine, threonine, methionine), cyclic (proline), armotaic (phenylalanine, tyrosine, tryptophan), basic (histidine, lysine, arginine), and acidic and amides (aspartate, glutamate, asparagine, glutamine). Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity.

CD30 (also known as TNFRSF8, human GeneID 943, see, e.g., NP_001234.3 for reference protein sequence and annotated domains; see homologene 949 for description of homologs) is a transmembrane glycoprotein with a molecular weight of 120 kDa of the tumor necrosis factor receptor family and tumor marker. This receptor is expressed by activated, but not by resting, T and B cells. It is a positive regulator of apoptosis, and also has been shown to limit the proliferative potential of autoreactive CD8 effector T cells and protect the body against autoimmunity. CD30 is associated with various lymphomas. CD30 is associated with anaplastic large cell lymphoma. CD30 is also expressed on classical Hodgkin Lymphoma Reed-Sternberg cells.

An "antibody-drug conjugate" or ADC, such as an anti-CD30 antibody-drug conjugate, is a macromolecular complex of an immunoglobulin, or fragment thereof comprising an antigen-binding domain, and a drug, such as an anti-neoplastic, where the immunoglobulin portion is connected to the drug by a linker moiety, which may, in certain embodiments, be covalently bonded to both the immunoglobulin region and drug and comprises a cleavable bond, e.g., so as to release the drug from the ADC at a suitable time. One particular anti-CD30 ADC useful in the methods provided by the invention is brentuximab vedotin.

A "body surface area-adjusted dose", sometimes abbreviated "BSA-adjusted dose", such as a non-adult (or pediatric) BSA-adjusted dose, is a drug dose, typically expressed as mg/m$^2$, adjusted to the approximate surface area of a subject, e.g., relative to a standard reference adult dose (such as an approved dosage), which is more accurate than a weight-adjusted dose (e.g., expressed in mg/kg). Body surface area can be estimated using the following formula: 0.20247×height (m)$^{0.725}$×weight (kg)$^{0.425}$. See, for example, Du Bois D, Du Bois E F (June 1916). "A formula to estimate the approximate surface area if height and weight be known". Archives of Internal Medicine 17 (6): 863-71. doi:10.1001/archinte.1916.00080130010002 and Verbraecken, J; Van de Heyning P; De Backer W; Van Gaal L (April 2006). "Body surface area in normal-weight, overweight, and obese adults. A comparison study". *Metabolism—Clinical and Experimental* 55 (4): 515-24.

A "hematological or lymphoid cancer" is a non-solid neoplasm predominantly present in blood, bone marrow, lymph, or lymphatic system. In particular embodiments, the cancer is Hodgkin lymphoma (HL), anaplastic large cell lymphoma (ALCL), systemic anaplastic large cell lymphoma (sALCL), diffuse large B-cell lymphoma (DLBCL), cutaneous T-cell lymphoma (CTCL), or mantle cell lymphoma (MTCL). In some embodiments, the hematological or lymphoid cancer is a lymphoma. Nonlimiting examples of lymphomas include Hodgkin lymphomas, B-cell lymphomas, T-cell lymphomas, natural killer (NK) cell neoplasms and immunodeficiency-associated lymphoproliferative disorders. Nonlimiting examples of Hodgkin lymphomas (HL) include nodular sclerosis HL, mixed cellularity HL, lymphocyte-rich HL, and lymphocyte depleted or not depleted HL. Nonlimiting examples of lymphomas other than Hodgkin lymphomas include, for example, low grade/follicular non-Hodgkin's lymphoma (NHL), follicular non-Hodgkin's lymphoma (NHL), small lymphocytic (SL) NHL, T or B prolymphocytic leukemia, diffuse large B cell lymphoma (DLBCL), peripheral T cell lymphomas (PTCL), PTCL-not otherwise specified (PTCL-NOS), mantle cell lymphoma, marginal zone lymphomas, mature T-cell lymphoma, B or T cell lymphoblastic lymphoma, Burkitt's lymphoma, primary thyroid lymphoma, Waldenstrom's Macroglobulinemia, lymphoplasmacytic lymphoma, mycosis fungoides, adult T-cell leukemia/lymphoma (ATLL), angioimmunoblastic lymphoma (AITL), enteropathy-associated T-cell lymphoma (EATL), and anaplastic large cell lymphoma (ALCL). It should be clear to those of skill in the art that these pathological conditions may often have different names due to differing/changing classification systems.

Although not considered hematological or lymphoid cancers, the kits and methods provided by the invention can also be used to treat a non-adult human subject with mycosis fungoides or systemic lupus erythematosus (SLE).

A "solid tumor" is an abnormal mass of tissue that usually does not contain cysts or liquid areas and in particular embodiments refers to neoplasms, as opposed to benign tumors. In certain embodiments, a solid tumor is a neoplasm that excludes hematological or lymphoid cancers as defined above. In some embodiments, the cancer is a solid tumor. Nonlimiting examples of solid tumors include ovarian cancer (e.g., ovarian epithelial carcinoma or ovarian serous carcinoma), skin cancer (e.g., melanoma and/or skin squamous cell carcinoma), breast cancer (e.g., triple negative breast cancer), thyroid cancer (e.g., anaplastic thyroid carcinoma), pancreatic cancer (e.g., undifferentiated pancreatic carcinoma or adenocarcinoma), lung cancer (e.g., small cell or squamous cell lung cancer), thymus cancer (e.g., thymic carcinoma), anal cancer (e.g., anal squamous cell carcinoma), endometrial cancer, uterine cancer, gynecologic carcinosarcomas, urethral cancer, genitourinary squamous cell carcinomas, carcinoma of unknown primary, Sertoli cell tumors, and leydig cell tumors. The solid tumor can be a primary or metastatic tumor.

In some embodiments, a disorder characterized by pathological activity of CD30+ cells that is treatable by the kits and methods provided by the invention is a cancer such as: ovarian cancer, skin cancer, breast cancer, thyroid carcinoma, pancreatic carcinoma, lung cancer, squamous cell lung cancer, anal cancer, uterine cancer, urethral cancer, endometrial cancer, carcinoma of unknown primary, thymic carcinoma, genitourinary squamous cell carcinomas, gynecologic carcinosarcomas, Sertoli cell tumors, leydig cell tumors, and pancreatic adenocarcinoma. In some embodiments, the ovarian cancer is ovarian serous carcinoma; the skin cancer is melanoma or skin squamous cell carcinoma; the breast cancer is triple negative breast cancer; the lung cancer is small cell lung cancer or squamous cell lung cancer, the thyroid carcinoma is anaplastic thyroid carcinoma; the pancreatic carcinoma is adenocarcinoma or undifferentiated pancreatic carcinoma; or the anal cancer is anal squamous cell carcinoma.

A "non-adult human" subject (sometimes referred to as a non-adult subject or pediatric subject) is less than 18 years old. In particular embodiments, the subject is between (inclusive) 17 and 2 years old, e.g., between 17 and 4 or 5 years old. In some embodiments, the subject is an adolescent, i.e., between about: 17 and 13 years old, e.g. between about: 17 and 12 years old, 16 and 12 years old, 16 and 13 years old, 15 and 12 years old, et cetera. In other embodiments, the subject is a pre-adolescent, e.g. less than about 13 years old, e.g., between about: 12 and 2 years old, 12 and 6 years old, 11 and 2 years old, 11 and 6 years old, 10 and 2 years old, 10 and 6 years old, et cetera. In some embodiments, the subject is 6 years old, or less, e.g., between about: 6 and 2 years old, 6 and 3 years old, 6 and 4 years old, 6 and 5 years old, 5 and 2 years old, 4 and 2 years old, or 3 and 2 years old. In certain embodiments, the non-adult human subject weighs less than about 50 kg, e.g., less than about: 50 kg, 49 kg, 48 kg, 47 kg, 46 kg, or 45 kg. In some embodiments, the non-adult human subject is between about: 50 and 12.5 kg, 50 and 16 kg, 45 and 12.5 kg, 45 and 16 kg, et cetera.

The methods provided by the invention can be practiced using the ADC as a front-line therapy alone or in combination with another treatment or therapeutic regimen, or as a follow-on therapy (e.g., as a second line, third line, retreatment, consolidation, or salvage therapy) after the subject has been treated with at least one treatment method or therapeutic regimen, where the prior treatment or therapeutic regimen may be successful, or not (e.g., relapse, refractory, or without significant initial response). Whether practiced as frontline, second line, third line, retreatment, consolidation, salvage or retreatment therapy, in the methods provided by the invention, the ADC can be used either as a monotherapy or in a combination therapy, (e.g., with an additional one, two, three, four agents, or more). A subject treated by the methods provided by the invention can, in some embodiments, also be undergoing treatment with a composition comprising hematopoietic stem cells (HSCs—either autologous or allogenic), such as bone barrow or a fraction thereof, which may, or may not, undergo culture expansion and/or enrichment. In certain embodiments, the subject may have previously received HSC therapy.

In the methods provided by the invention, the anti-CD30 antibody-drug conjugate (ADC) can be administered to the non-adult human subject at a body surface area-adjusted dose relative to any effective adult dose (e.g., a weight-adjusted dose). In some embodiments, the non-adult subject's normalized drug expose as measured by area under the ADC concentration time curve (AUC) is substantially similar to an adult AUC for an indicated adult dose. In certain embodiments, the ADC is administered at a dose of between about: 32-78 mg/m$^2$. In certain particular embodiments, the dose is about: 64-78 mg/m$^2$, e.g. between about: 66-76 mg/m$^2$, 68-74 mg/m$^2$, 70-72 mg/m$^2$, or about 71.5 mg/m$^2$. In more particular embodiments, the ADC is administered at a dose of between about: 70-72 mg/m$^2$, 71-72 mg/m$^2$, or about 71.5 mg/m$^2$. In other particular embodiments, the ADC is administered at a dose of about: 43-53 mg/m$^2$, e.g., between about: 45-51 mg/m$^2$, 47-49 mg/m$^2$, or about 48 mg/m$^2$. In still other particular embodiments, the ADC is administered at a dose of about: 32-40 mg/m$^2$, e.g. between about: 34-38 mg/m$^2$, 35-37 mg/m$^2$, or about 36 mg/m$^2$. Numerous regimens using these doses are encompassed by the methods provided by the invention and are described, inter alia, below. For example, in some embodiments, the doses may be administered every two weeks (e.g., about 43-53 mg/m$^2$ (e.g. between about: 45-51 mg/m$^2$, 47-49 mg/m$^2$, or about 48 mg/m$^2$) or about 32-40 mg/m$^2$ (e.g., between about: 34-38 mg/m$^2$, 35-37 mg/m$^2$, or about 36 mg/m$^2$) every two weeks), or every three weeks (e.g., about: 64-78 mg/m$^2$ (e.g. between about: 66-76 mg/m$^2$, 68-74 mg/m$^2$, 70-72 mg/m$^2$, or about 71.5 mg/m$^2$) every three weeks).

In some embodiments, a subject treated by the methods provided by the invention is undergoing concurrent chemotherapy, such as with AVD (adriamycin, vinblastine, dacarbazine), CHP (doxorubicin, cyclophosphamide, prednisone), RCHOP (doxorubicin, cyclophosphamide, prednisone, vincristine), rituximab+bendamustine, nivolumab, radio therapy, HSC therapy, or a combination of the foregoing. These concurrent therapies may be substantially concurrent or sequential, where the ADC treatment may be administered either before or after the additional therapies. AVD chemotherapy regimens are known in the art and, in some embodiments, entail the following doses: adriamycin (25 mg/m$^2$, e.g., by IV bolus), vinblastine (6 mg/m$^2$, e.g., by IV infusion), dacarbazine (375 mg/m$^2$, e.g., by IV infusion). Similarly, CHP (doxorubicin, e.g. 50 mg/m$^2$ every 3 weeks by IV infusion for 6-8 cycles; prednisone, e.g. 100 mg on Days 1 to 5 of each 3-week cycle, orally for 6-8 cycles; cyclophosphamide, e.g., 750 mg/m$^2$ every 3 weeks by IV infusion for 6-8 cycles), RCHOP (doxorubicin, e.g. 50 mg/m$^2$ every 3 weeks by IV infusion for 6-8 cycles; prednisone, e.g. 100 mg on Days 1 to 5 of each 3-week cycle, orally for 6-8 cycles; vincristine, e.g., 1.4 mg/m$^2$ (maximum 2 mg) every 3 weeks by IV infusion for 6-8 cycles; cyclophosphamide, e.g., 750 mg/m$^2$ every 3 weeks by IV infusion for 6-8 cycles), rituximab+bendamustine (e.g., IV infusions of rituximab on day 1 or day 2 and bendamustine on both days 1 and 2 of each 21 day cycle; e.g., IV infusions of brentuximab vedotin followed by bendamustine on day 1, and rituximab followed by bendamustine on day 2 of each 21 day cycle), and nivolumab (e.g., 3 mg/kg by intravenous (IV) infusion, e.g., every 14 days, e.g. for up to 4, 10, 14, 15, 20, 25, or 30 cycles), treatments are known, with the foregoing dosings being exemplary only. These doses are, in some embodiments, administered every one, two or three weeks (in particular embodiments every two weeks), e.g., for two treatments per 28 day cycle. Subjects being treated by, e.g., AVD, CHP, RCHOP, rituximab+bendamustine, or nivolumab therapy may receive one, two, three, four, five, six, seven, eight, nine, ten, or more, cycles. Additional combination therapies that can be adapted according to the methods provided by the invention, i.e., for BSA dose-adjusted include the combination of anti-CD30 ADCs and aurora kinase inhibitors, as described in WO/2015/085289, which is herein incorporated by reference in its entirety.

In certain embodiments, as noted above, the ADCs for the kits and methods provided by the invention comprises an anti-CD30 antibody that is substantially similar to cAC10 (the antibody backbone of brentuximab vedotin) or a related antibody of cAC10. cAC10 is a chimeric antibody that binds the CD30 protein (human GeneID 943; protein reference sequence NP_001234.3). cAC10 is described in WO2002/043661 (see also U.S. Pat. No. 7,090,843), while certain particular conjugates that can be made with cAC10 are described in WO2004/010957 (see also U.S. Pat. No. 7,659,241). The structure of brentuximab vedotin, as well as particular dosing regimens of it, are described in WO2010081004 (also published as US20110268751A1, see claim 17; see also U.S. Pat. No. 9,211,319). The foregoing references are incorporated by reference for, inter alia, their description of cAC10, ADCs containing it (e.g., with an auristatin, as in brentuximab vedotin), and formulations of, and modes of administering, the same. In particular embodiments, the anti-CD30 antibody comprises the complementarity determining regions (CDRs) of cAC10 and, in some more particular embodiments, the anti-CD30 antibody is cAC10. While a variety of toxic payloads can be present in the ADCs for use in the kits and methods provided by the invention, in some embodiments, the ADC comprises an auristatin. In some more particular embodiments, the auristatin is monomethyl auristatin E (MMAE). In other embodiments, the drug moiety is dovaline-valine-dolaisoleunine-dolaproine-phenylalanine (MMAF). The drug and anti-CD30 antibody can be conjugated by any suitable means. In certain embodiments, the ADC comprises a cathepsin cleavable linker, optionally including a spacer. In more particular embodiments, the cathepsin cleavable linker is a valine-citrulline linker. In more particular embodiments, the ADC is brentuximab vedotin.

The kits and methods provided by the invention are adapted for treating non-adult human subjects with BSA-adjusted doses, according to treatment schedules for adult subjects. Thus, in some embodiments of the methods provided by the invention, the ADC is administered for more than one cycle (dose), e.g., 2, 3, 4, 5, 6, 7, 8, 9, 10, 11, 12, 13, 14, 15, 16, 17, 18, 19, or 20 cycles, or more, e.g., once every one, two, three, four, five, or six weeks, e.g., once every two or three weeks. Thus, in certain embodiments, a cycle of treatment entails administering a dose every 14 days, e.g., for one, two, three, four, five, six, seven, eight, nine, ten, or more, cycles. In other embodiments a cycle of treatment entails administering a dose every 21 days, e.g., for one, two, three, four, five, six, seven, eight, nine, ten, or more, cycles.

The present invention contemplates administration of the ADC for one or more treatment cycles, for example, 1, 2, 3, 4, 5, 6, 7, 8, 9, 10, 11, 12, 13, 14, 15, 16, 17, 18, 19, 20, or more, treatment cycles. In some embodiments, there will be periods of rest between one or more of the treatment cycles. For example, in some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the antibody-drug conjugate once during a treatment schedule, e.g., on day 1 of a 21 day cycle, twice during a treatment cycle, e.g., on days 1 and 15 of a 21 day cycle or on days 1 and 15 of a 28 day cycle, and three times during a treatment cycle, e.g., on days 1, 8 and 15 of a 21 day cycle or on days 1, 8 and 15 of a 28 day cycle. Other dosage schedules are encompassed by the present invention.

The present invention encompasses treatment schedules wherein the antibody-drug conjugate is administered once during a treatment cycle, e.g., a 1, 2, 3 or 4 week time period. For example, in some embodiments, the antibody-drug conjugate will be administered on the first day of a 2, 3 or 4 week treatment cycle, e.g., on day 1 of a three or four week cycle. In some embodiments, the antibody-drug conjugate will be administered on day 1 of a 3 or 4 week treatment cycle, or on any other day of a two, three or four week treatment cycle.

In other embodiments the antibody-drug conjugate will be administered more than once during a treatment cycle. For example, in some embodiments, the antibody-drug conjugate will be administered weekly for three consecutive weeks in a three or four week treatment cycle. For example, in some embodiments, the antibody-drug conjugate will be administered on days 1, 8 and 15 of each 21 day treatment cycle. In some embodiments, the antibody-drug conjugate will be administered on days 1, 8, and 15 of each 28 day treatment cycle.

In even other embodiments, the antibody-drug conjugate will be administered every two weeks in a four week treatment cycle. For example, in some embodiments, the antibody-drug conjugate compound will be administered on days 1 and 15 of each 28 day treatment cycle.

The dosage of the antibody-drug conjugate administered to a patient will also depend on frequency of administration. The present invention contemplates antibody-drug conjugate delivery once during the treatment cycle or by a split delivery.

The present invention encompasses embodiments wherein the antibody-drug conjugate compound will be administered, in a non-adult human (pediatric) BSA-adjusted dose, relative to a dose range in an adult of: 0.1 mg/kg to 2.7 mg/kg of the subject's body weight per dose, 0.5 mg/kg to 2.0 mg/kg of the subject's body weight per dose, 0.9 mg/kg to 2.0 mg/kg of the subject's body weight per dose, and 0.9 mg/kg to 1.8 mg/kg of the subject's body weight per dose. Other ranges are encompassed by the present invention as long as they produce the desired result. In one embodiment, the antibody-drug conjugate will be administered, in a non-adult human BSA-adjusted dose, relative to a dose range in an adult of about 1.2 mg/kg of the subject's body weight per dose. In another embodiment, the antibody-drug conjugate compound will be administered, in a non-adult human BSA-adjusted dose, relative to a dose range in an adult of about 1.8 mg/kg of the subject's body weight per dose. In yet another embodiment, the antibody-drug conjugate compound will be administered, in a non-adult human BSA-adjusted dose, relative to a dose range in an adult of about 0.9 mg/kg of the subject's body weight per dose.

The present invention encompasses treatment schedules wherein the total dosage of the antibody-drug conjugate is administered, in a non-adult human BSA-adjusted dose, relative to a dose range in an adult of, for example, 0.1 mg/kg to 5 mg/kg, 0.1 mg/kg to 4 mg/kg, 0.1 mg/kg to 3.2 mg/kg, or 0.1 mg/kg to 2.7 mg/kg of the subject's body weight over a treatment cycle, e.g., a 3 or 4 week time period. In some embodiments, the total dosage of the antibody-drug conjugate administered, in a non-adult human BSA-adjusted dose, is relative to a dose range in an adult of, for example, about 0.6 mg/kg to about 5 mg/kg, about 0.6 mg/kg to about 4 mg/kg, about 0.6 mg/kg to about 3.2 mg/kg, about 0.6 mg/kg to about 2.7 mg/kg, or even about 0.9 mg/kg to about 3.0 mg/kg over a treatment cycle, e.g., a 3 or 4 week time period. In some embodiments, the dosage, in a non-adult human BSA-adjusted dose, relative to a dose range in an adult of about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, or about 3.8 mg/kg of the subject's body weight over the treatment cycle, e.g., a 3 or 4 week time period. In some embodiments, the total dosage of the antibody-drug conjugate, administered, in a non-adult human BSA-adjusted dose, is relative to a dose range in an adult of 1.8 mg/kg of the subject's body weight over a treatment cycle, e.g., a 3 or 4 week time period. In some embodiments, the total dosage of the antibody-drug conjugate compound, administered to a patient will be 2.4 mg/kg of the subject's body weight over a treatment cycle, e.g., a 3 or 4 week time period. In some embodiments, the total dosage of the antibody-drug conjugate compound, administered, in a non-adult human BSA-adjusted dose, is relative to a dose range in an adult of 3.6 mg/kg of the subject's body weight over a treatment cycle, e.g., a 3 or 4 week time period. In some embodiments, the antibody-drug conjugate will be administered, in a non-adult human BSA-adjusted dose, relative to a dose range in an adult of 1.2 mg/kg of the subject's body weight over a treatment cycle, e.g., a 3 or 4 week time period. In some embodiments, the antibody-drug conjugate compound will be administered, in a non-adult human BSA-adjusted dose, relative to a dose range in an adult of 1.8 mg/kg of the subject's body weight over a treatment cycle, e.g., a 3 or 4 week time period. In some embodiments, the antibody-drug conjugate compound will be administered, in a non-adult human BSA-adjusted dose, relative to a dose range in an adult of 0.9 mg/kg of the subject's body weight over a treatment cycle, e.g., a 3 or 4 week time period.

The foregoing adult doses can readily be converted to BSA-adjusted human pediatric doses using one or both of the reference values of 0.9 mg/kg (36 mg/m$^2$), 1.2 mg/kg (48 mg/m$^2$), or 1.8 mg/kg (71.5 mg/m$^2$) by interpolation.

The antibody-drug conjugate can be administered by any method known to one skilled in the art. For example, the antibody-drug conjugate can be administered in the form of a composition, in some embodiments a pharmaceutical composition of an antibody-drug conjugate and a pharmaceutically acceptable carrier, such as those described herein. In some embodiments, the pharmaceutical composition is a lyophilized powder, which when reconstituted, can be administered via an intravenous route, such as intravenous injection or intravenous infusion. In some embodiments, the antibody-drug conjugate is administered via intravenous injection. In some embodiments, the antibody-drug conjugate is administered via intravenous infusion. In another embodiment brentuximab vedotin is administered via intravenous infusion.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. Remington: The Science and Practice of Pharmacy, 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, *Remington's Pharmaceutical Science,* 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

EXEMPLIFICATION

Example 1: Phase 1/2 Study of Brentuximab Vedotin in Pediatric Patients with Relapsed or Refractory (R/R) Hodgkin Lymphoma (HL) or Systemic Anaplastic Large-Cell Lymphoma (sALCL)

The pediatric study was designed as a phase 1/2, open-label, single-agent, multicenter, dose-escalation study of brentuximab vedotin (BV) in pediatric patients with relapsed or refractory systemic anaplastic large-cell lymphoma (ALCL) or Hodgkin's lymphoma (HL) for which standard, curative, life-prolonging, or palliative treatment did not exist or was no longer effective. This study had assessment of pharmacokinetics of BV in pediatric patients as one of its objectives.

The goal of phase 1 portion of the study was to establish safety and define MTD (maximum tolerated dose) of brentuximab vedotin in pediatric hematological malignancies with high expression of CD30, both HL and ALCL were included in the phase 1 study population. The phase 2 study was designed to administer brentuximab vedotin at the RP2D (recommended phase II dose) determined as the MTD [Maximum Tolerated Dose] in the phase 1 portion of the study.

Blood samples for determining BV levels from the serum were obtained at several time points during treatment with BV at the dose of 1.4 or 1.8 mg/kg body weight every 3 weeks. These doses were within the range of doses that were previously determined to be safe and efficacious in the adult population in earlier studies (Younes, et al., *N. Engl J Med* 363; 19, Nov. 2010).

The pharmacokinetic analyses described here included pharmacokinetic data from 30 pediatric patients for the initial analyses.

Upon analysis of the systemic exposure to BV in the pediatric population, it was found that decrease in age from about 18 years led to decrease systemic exposure to BV as measured by the Area Under the concentration-time Curve (AUC), microgram/ml*day. See FIG. 1A. This relationship was found to regress better with body weight. Since the original dosing schedule was body weight based and supposed to have normalized exposure over the pediatric body size range, further analysis based on population pharmacokinetics was performed to determine how the pediatric patients should be dosed to allow them to have similar exposures as seen in the adult.

Figure 1B:
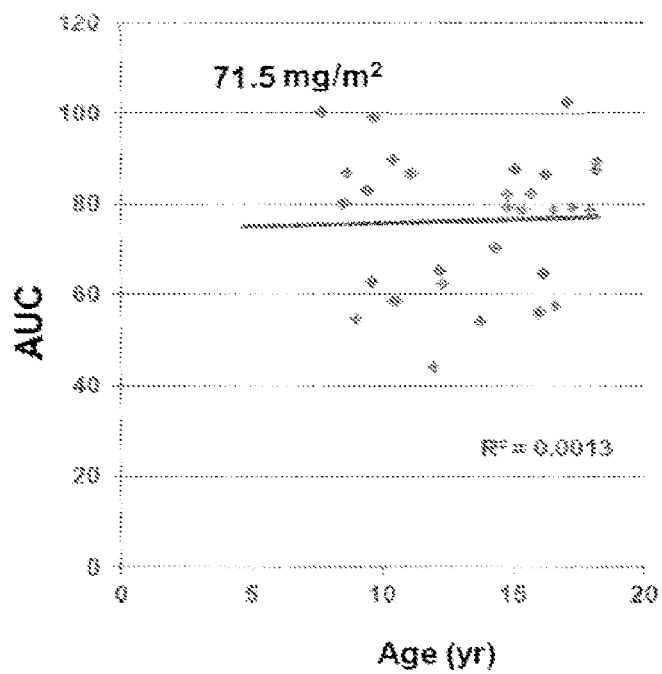

The population PK (pharmacokinetic) modeling used PK data from the C25002 pediatric study described above, and an adult patient study (*N. Engl. J. Med* 363; 19, Nov. 2010). In that analysis body surface area was a significant covariate of brentuximab vedotin exposure. Simulation procedures established dosing based on BSA will normalize systemic exposure to BV in children of various body weights and hence, different age group, FIG. 1B. Thus as an example, simulation analysis showed that brentuximab vedotin dosed at 71.5 mg/m$^2$ provided pediatric patients in the lower-body weight range AUC more similar to that seen in the adult population dosed with BV at 1.8 mg/kg. Since BV has shown linear pharmacokinetics, it is reasonable to extrapolate various mg/m$^2$ dose equivalent from the relationship between 1.8 mg/kg to 71.5 mg/m$^2$.

Example 2: Treating Pediatric Patients with Relapsed or Refractory (R/R) Hodgkin Lymphoma (HL) or Systemic Anaplastic Large-Cell Lymphoma (sALCL) with Brentuximab Vedotin Using Body Surface Area Based Dosing Regimen Pediatric (non adult human) patients with relapsed or refractory (r/r) Hodgkin Lymphoma (HL) or systemic anaplastic large-cell lymphoma (sALCL) for which standard, curative, life-prolonging, or palliative treatment does not exist or is no longer effective are provided and are administered brentuximab vedotin (BV), except dosing is adjusted to body surface area (BSA) instead of body weight. Pediatric study subjects are administered BV (administered IV infusion, once every three weeks (21 days)) at a dose of 71.5 mg/m$^2$. Each 21-day treatment cycle is composed of 1 day study drug treatment, followed by a monitoring period of 20 days. Patients may receive BV for up to 16 cycles. Objective response rates (ORR; complete remission (CR)+ partial remission (PR)) are determined by an independent review facility (IRF) using PET, CT, MRI and, clinical assessment according to the International Working Group (IWG) Revised Response Criteria for Malignant Lymphoma. Time to progression (from the first dose of study treatment to the date of first documented progressive disease), time to response (from the first dose of study treatment to the date of first documentation of a complete or partial response), duration of response (from the date of first documentation of a response to the date of progressive disease), event-free survival (from first dose until treatment failure), progression-free survival (PFS; from the first dose of study treatment to disease progression or death), and overall survival (OS; from the first dose of study treatment to date of death) are also evaluated. Patients are followed for progression-free survival (PFS) and overall survival (OS) every 12 weeks for 12 months after the end of treatment (EOT) visit. Thereafter, assessment for OS will continue every 6 months until the sooner of death or study closure or a maximum of 2 years after enrolment of the last patient. Relative to treatments without BV, pediatric patients treated with BV exhibit one or more of improved CR, PR, PFS, or OS. Pediatric patients treated with BSA-adjusted doses of BV also exhibit one or more of improved CR, PR, PFS or OS relative to pediatric subjects treated with BV, at a weight-adjusted dose of 1.8 mg/kb.

Example 3: Treating Pediatric Patients with Advanced Classical Hodgkin Lymphoma with Brentuximab Vedotin+AVD Using Body Surface Area Based Dosing Regimen Pediatric (non adult human) patients diagnosed with advanced classical Hodgkin Lymphoma are provided. Study subjects are randomly assigned to and administered one of the following treatments: 1) brentuximab vedotin (BV) administered at a dose of 48 mg/m$^2$ by IV infusion on Days 1 and 15 of each 28-day cycle, together with AVD (adriamycin 25 mg/m$^2$, vinblastine 6 mg/m$^2$, and dacarbazine (DTIC) 375 mg/m$^2$, each administered by IV infusion on Days 1 and 15 of each 28-day cycle); or 2) ABVD (doxorubicin 25 mg/m$^2$, bleomycin 10 units/m$^2$, vinblastine 6 mg/m$^2$, and dacarbazine (DTIC) 375 mg/m$^2$, each administered by IV infusion on Days 1 and 15 of each 28-day cycle).

Modified progression free survival (mPFS) is determined per independent review facility (IRF) (date of randomization to mPFS event, for approximately 3 to 5 years). Overall survival (OS) rate is also assessed (date of randomization to the date of death, for approximately 5 to 7 years). Relative to treatment with ABVD, pediatric patients treated with BV+AVD exhibit one or more of improved mPFS or OS.

Example 4: Treating Pediatric Patients with CD30-Positive Mature T-Cell Lymphomas with Brentuximab Vedotin+CHP Using Body Surface Area Based Dosing Regimen Pediatric (non adult human) patients with CD30-positive mature t-cell lymphomas (Anaplastic Large-Cell Lymphoma, Non-Hodgkin Lymphoma, T-Cell Lymphoma) are provided. Study subjects are randomly assigned to one of the following treatments: 1) BV (administered IV, once every three weeks (21 days)) at a dose of 71.5 mg/m$^2$ for 6-8 cycles together with CHP (cyclophosphamide 750 mg/m$^2$ every 3 weeks by IV infusion for 6-8 cycles, doxorubicin 50 mg/m$^2$ every 3 weeks by IV infusion for 6-8 cycles, prednisone 100 mg on Days 1 to 5 of each 3-week cycle, orally for 6-8 cycles) chemotherapy); or 2) CHOP chemotherapy (doxorubicin 50 mg/m$^2$ every 3 weeks by IV infusion for 6-8 cycles, prednisone 100 mg on Days 1 to 5 of each 3-week cycle, orally for 6-8 cycles, vincristine 1.4 mg/m$^2$ (maximum 2 mg) every 3 weeks by IV infusion for 6-8 cycles, and cyclophosphamide 750 mg/m$^2$ every 3 weeks by IV infusion for 6-8 cycles)).

Progression-free survival is determined by an independent review facility (IRF) (until disease progression, subsequent anticancer chemotherapy, death, or study closure, up to 5 years post-treatment). Complete remission (CR), overall survival (OS), and objective response rate (ORR), each per IRF are also evaluated.

Relative to treatment with CHOP patients treated with BV+CHP exhibit one or more of improved PFS, OS or ORR.

Example 5: Treating Pediatric Patients with CD30-Positive Cutaneous T-Cell Lymphoma with Brentuximab Vedotin Using Body Surface Area Based Dosing Regimen Pediatric (non adult human) patients with CD30-positive cutaneous t-cell lymphomas (Primary Cutaneous Anaplastic Large Cell Lymphoma, Mycosis Fungoides, Cutaneous T-Cell Lymphoma) are provided. Study subjects are randomly assigned to one of the following treatments: 1) BV (administered IV, once every three weeks (21 days)) at a dose of 71.5 mg/m$^2$ as monotherapy for up to a total of 16 cycles; or 2) physician's choice of methotrexate or bexarotene (methotrexate is administered orally (5 to 50 mg) once weekly; dose adjustment is guided by patient response and toxicity or bexarotene is administered orally (300 mg/m$^2$) once daily with meals).

The proportion of patients achieving an objective response (ORR; complete remission (CR)+partial remission (PR)) that lasts at least 4 months is evaluated. The proportion of patients achieving complete response (CR) and progression-free survival (PFS) are also evaluated.

Relative to treatments with either methotrexate or bexarotene, patients treated with BV exhibit one or more of improved ORR, CR or PFS.

Example 6: Treating Pediatric Participants with Advanced Stage Newly Diagnosed Hodgkin Lymphoma with a Body Surface Area Based Dosing Regimen of Brentuximab Vedotin, Together with Adriamycin, Vinblastine, and Dacarbazine Pediatric subjects with advanced stage (Stage III and Stage IV disease) newly diagnosed Hodgkin Lymphoma (HL; histologically confirmed CD30+ classical HL; treatment-naive) are provided in a study assessing the safety and feasibility of combining brentuximab vedotin (BV) with a multiagent chemotherapy regiment that is based on a current standard of care (SOC) first-line treatment regimen for newly diagnosed HL, and evaluating the anti-tumor activity of this combination.

The study is conducted in 2 phases, Phase 1 and Phase 2. In Phase 1, brentuximab vedotin (BV) is administered to the subjects at a dose of 48 milligram per square meter (mg/m$^2$) or 36 mg/m$^2$ by intravenous infusion, once on Day 1 and 15 of each 28-day cycle. This administration is after approximately 1 hour of doxorubicin 25 mg/m$^2$, vinblastine 6 mg/m$^2$, and dacarbazine 375 mg/m$^2$, administered to the subjects by intravenous infusion, once on Day 1 and 15 of each 28-day cycle for up to 6 cycles.

Where the first 6 subject complete a dose limiting toxicity (DLT) observation with 0 or 1 subjects experiencing a DLT, 48 mg/m$^2$ is established as the recommended dose of BV for Phase 2 of the study. If at any time more than 1 subject out of a maximum 6 DLT-evaluable subjects experiences a DLT, BV dose is reduced to 36 mg/m$^2$ using the same dosing schedule as described, supra. In Phase 2, BV is administered at the established recommended dose for Phase 2 using the same dosing schedule as Phase 1.

Subjects are evaluated to determine, inter alia, one or more of: the recommended dose of BV in combination with doxorubicin, vinblastine, and dacarbazine in a pediatric population; percentage of subjects who experience adverse events (AEs) (e.g., from the first dose of protocol therapy through 30 days after administration of the last dose of protocol therapy); percentage of subjects who experience serious adverse events (SAEs)(e.g., from the first dose of protocol therapy through 30 days after administration of the last dose of protocol therapy); percentage of subjects who achieve a complete remission (CR) (e.g., per Independent Review Facility (IRF) assessment at end of treatment (EOT) per International Working Group (IWG) criteria); percentage of subjects whose disease is Positron Emission Tomography (PET) negative after 2 cycles of protocol therapy (e.g., per IRF assessment); percentage of subjects who achieve a partial remission (PR) (e.g. per IRF assessment at EOT per IWG criteria); percentage of subjects who achieve an overall response (OR) (e.g., per IRF assessment at EOT per IWG criteria); percentage of subjects in the response-evaluable population who are able to complete six 28-day cycles of treatment at the recommended dose.

Subjects treated with BV in combination with adriamycin, vinblastine, and dacarbazine exhibit one or more of: an acceptable percentage of subjects experiencing AEs and SAEs; a significant percentage of subjects exhibiting: CR, PET negative disease, PR, OR, and completion of 6 cycles of therapy.

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or other accession numbers (typically referencing National Center for Biotechnology Information (NCBI) accession numbers), including, for example, genomic loci, genomic sequences, functional annotations, allelic variants, and reference mRNA (including, e.g., exon boundaries or response elements) and protein sequences (such as conserved domain structures), Homologene, OMIM, as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The foregoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

The invention claimed is:

1. A method of treating a hematological or lymphoid cancer in a non-adult human subject comprising administering to the subject brentuximab vedotin at a body surface area adjusted dose of 71.5 mg/m$^2$, wherein the hematological or lymphoid cancer expresses CD30.

2. The method of claim 1, wherein the brentuximab vedotin is administered once every three weeks.

3. The method of claim 1, wherein the cancer is Hodgkin lymphoma, anaplastic large cell lymphoma (ALCL), peripheral T cell lymphoma (PTCL), cutaneous T-cell lymphoma (CTCL), or mantle cell lymphoma (MTCL).

4. The method of claim 3, wherein the cancer is relapsed or refractory Hodgkin lymphoma.

5. The method of claim 3, wherein the cancer is systemic anaplastic large cell lymphoma (sALCL).

6. The method of claim 1, wherein the brentuximab vedotin is administered on day 1 of a 21-day cycle, wherein the non-adult human subject is about 5 to about 17 years old.

7. The method of claim 1, wherein the subject is on a concurrent chemotherapy.

8. The method of claim 7, wherein the concurrent chemotherapy comprises adriamycin-vinblastine-dacarbazine (AVD), doxorubicin-cyclophospham ideprednisone (CHP), an immunotherapy, a hematopoietic stem cell transplant therapy, a radio therapy, or any combination thereof.

9. The method of claim 8, wherein the concurrent chemotherapy comprises AVD and/or CHP.

10. The method of claim 1, wherein the non-adult human subject is about 5 to about 17 years old.

11. The method of claim 1, wherein the brentuximab vedotin is administered for more than one treatment cycle.

12. The method of claim 11, wherein the brentuximab vedotin is administered for up to 16 treatment cycles.

13. The method of claim 12, wherein the brentuximab vedotin is administered for 16 treatment cycles.

14. The method of claim 12, wherein the brentuximab vedotin is administered for 9 treatment cycles.

* * * * *